(12) United States Patent
Caliskan et al.

(10) Patent No.: US 11,073,485 B2
(45) Date of Patent: Jul. 27, 2021

(54) METHOD AND APPARATUS FOR CT SCANNING OF LONGER WHOLE CORES

(71) Applicant: Saudi Arabian Oil Company, Dhahran (SA)

(72) Inventors: Sinan Caliskan, Dhahran (SA); Abdullah Shebatalhamd, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/802,164

(22) Filed: Feb. 26, 2020

(65) Prior Publication Data

US 2020/0191731 A1 Jun. 18, 2020

Related U.S. Application Data

(63) Continuation of application No. 15/987,004, filed on May 23, 2018.

(51) Int. Cl.
*G01N 23/046* (2018.01)
*G01N 33/24* (2006.01)

(52) U.S. Cl.
CPC ......... *G01N 23/046* (2013.01); *G01N 33/241* (2013.01); *G01N 2223/3308* (2013.01)

(58) Field of Classification Search
CPC .... F16C 13/04; F16C 2316/10; F16C 29/045; G01N 2223/309; G01N 2223/3308; G01N 2223/616; G01N 23/046; G01N 33/241
See application file for complete search history.

(56) References Cited

U.S. PATENT DOCUMENTS

| 2,166,608 A | 7/1939 | Postlewaite |
| 2,641,428 A | 6/1953 | Kirk et al. |
| 2,859,349 A | 11/1958 | Bradley et al. |

(Continued)

FOREIGN PATENT DOCUMENTS

| CN | 201339654 Y | 11/2009 |
| CN | 203197012 U | 9/2013 |

(Continued)

OTHER PUBLICATIONS

International Search Report and Written Opinion for International Application No. PCT/2019/033115 (SA5877) report dated Sep. 26, 2019; pp. 1-15.

*Primary Examiner* — Marcus H Taningco
(74) *Attorney, Agent, or Firm* — Bracewell LLP; Constance G. Rhebergen; Brian H. Tompkins (57) ABSTRACT

Embodiments of the disclosure include an extended length core sample scanning apparatus that enables the imaging of extended length core samples using medical-type CT scanners. The extended length core sample scanning apparatus has a frame that defines a U-shaped receptacle that receives core housing containing the core sample when the core sample is placed in a CT scanner. The extended length core sample scanning apparatus may have two or more rollers located in the U-shaped receptacle to enable translation of the extended length core sample through a CT scanner during scanning. The rollers may also provide for a minimum clearance between the core housing and the walls of the U-shaped receptacle. Methods of imaging an extended length core sample are also provided.

8 Claims, 6 Drawing Sheets

(56) References Cited

U.S. PATENT DOCUMENTS

| | | |
|---|---|---|
| 4,710,946 A | 12/1987 | Hinch et al. |
| 4,854,163 A | 8/1989 | Mount, II et al. |
| 5,201,219 A | 4/1993 | Bandurski et al. |
| 5,275,563 A | 1/1994 | Cohen et al. |
| 7,010,085 B2 | 3/2006 | Kröner et al. |
| 7,082,185 B2 | 7/2006 | Freifeld et al. |
| 7,430,931 B2 | 10/2008 | Zamfes |
| 7,802,921 B2 | 9/2010 | Wu et al. |
| 8,422,626 B2 | 4/2013 | Jin et al. |
| 9,573,434 B2 | 2/2017 | Boot et al. |
| 2002/0104163 A1 | 8/2002 | Reimann |
| 2008/0232541 A1* | 9/2008 | Kang .................... G01V 5/005 378/10 |
| 2010/0324868 A1 | 12/2010 | Russell et al. |
| 2014/0251033 A1 | 9/2014 | Unno |
| 2016/0054239 A1 | 2/2016 | Schlecht et al. |
| 2016/0131793 A1* | 5/2016 | Szudajski ............ G01V 5/0025 378/53 |
| 2019/0351804 A1 | 11/2019 | Kanck et al. |

FOREIGN PATENT DOCUMENTS

| | | |
|---|---|---|
| CN | 104297267 A | 1/2015 |
| CN | 106290418 A | 1/2017 |
| WO | 2017004132 A1 | 1/2017 |

* cited by examiner

METHOD AND APPARATUS FOR CT SCANNING OF LONGER WHOLE CORES

CROSS-REFERENCE TO RELATED APPLICATIONS

This application is a continuation of and claims priority from U.S. Non-provisional application Ser. No. 15/987,004 filed May 23, 2018, and titled "METHOD AND APPARATUS FOR CT SCANNING OF LONGER WHOLE CORES," a copy of which is incorporated by reference in its entirety for purposes of United States patent practice.

BACKGROUND

Field of the Disclosure

The present disclosure generally relates to analyzing core samples from geological formations. More specifically, embodiments of the disclosure relate to methods and systems for using medical-type computed tomography (CT) scanners to analyze longer whole core samples.

Description of the Related Art

Wells may be drilled into rocks to access fluids stored in geological formations having hydrocarbons. Such a geological formation may be referred to as a "reservoir." A variety of techniques exist for determining the presence and amount of hydrocarbons in such reservoirs. In some instances, a sample of rock (referred to as a "core sample") and fluids may be collected downhole in the wellbore of the well and retrieved to the surface for further analysis. The core sample may be analyzed to determine various properties of the well, such as quantifying the amount and value of hydrocarbons (for example, oil and gas) in the reservoir. The analysis of a core sample may also determine the rate at which the identified oil and gas may be produced and aid in identifying techniques for extracting the oil and gas and maximizing recovery from the reservoir.

SUMMARY

Core samples may be analyzed non-destructively by computed tomography (CT) to obtain images of the core samples. In some instances, medical-type CT scanners with fixtures to enable the central positioning of core samples may be used to analyze core samples. A medical-type CT scanners refers to a CT scanner typically used for medical diagnostic imaging. However, the medical-type CT scanners with fixtures for core sample CT scanning purposes may have limited scanning capability with regard to the length of the core samples, such that these CT scanners are limited to core samples 3 feet (ft) or less in length and are unable to accommodate longer core samples (for example, core samples of 5 ft or 6 ft in length). Such longer core samples are referred to in the disclosure as "extended length core samples." Existing medical-type CT scanners with fixtures for core samples are unable to scan longer core samples without cutting the longer core samples into shorter pieces and damaging and altering the reservoir state of the core sample. Consequently, the cut core samples may produce inaccurate analysis of the reservoir state.

Additionally, the cutting of longer core samples to enable scanning with medical-type CT scanners is time-consuming and increases costs of the analysis of the core samples. Recent core sample techniques, such as sponge cores, may produce longer core samples that are required to be split into two pieces in order to perform CT scanning by existing medical-type CT scanners equipped with fixtures for core samples.

In one embodiment, an apparatus for computed tomography (CT) imaging of a core sample is provided. The apparatus includes a body configured to be coupled to a stationary table, the body defining a U-shaped receptacle configured to receive a core housing containing a core sample. The apparatus further includes a first roller located at a first position in the U-shaped receptacle and a second roller located at a second position in the U-shaped receptacle. The first roller and second roller are configured to support a weight of the core housing containing the core sample and define a clearance between the core housing and an interior wall of the U-shaped receptacle, such that a rotation of the rollers enables a translation of the core housing through the U-shaped receptacle.

In some embodiments, the first position is defined by an angle of about 45° with respect to a vertical axis and a horizontal axis of the body. In some embodiments, the second position is defined by an angle of about 45° with respect to a vertical axis and a horizontal axis of the body. In some embodiments, the clearance comprises at least 5 millimeter (mm). In some embodiments, the core sample has a length greater than 3 feet. In some embodiments, the core sample has a length of up to 6 feet. In some embodiments, the body is coupled to a support having at least two walls extending in the direction of translation. In some embodiments, the U-shaped receptacle has a width of 229 millimeters (mm) at a top of the U-shaped receptacle.

In another embodiment, a method of imaging a core sample is provided. The method includes placing a core sample in a computed tomography (CT) scanner. The placing includes placing a first end of a core housing containing the core sample to a CT scanning table located at a first side of the CT scanner, the CT scanning table configured to translate the core sample through the CT scanner, and placing a second end of the core housing containing the core sample in a U-shaped receptacle of a core sample scanning apparatus located at a second side of the CT scanner. The core sample scanning apparatus includes a body defining a U-shaped receptacle, the U-shaped receptacle configured to receive the core housing. The core sample scanning apparatus further includes a first roller located at a first position on the U-shaped receptacle and a second roller located at a second position on the U-shaped receptacle, the first roller and second roller configured to support a weight of the core housing containing the core sample and define a clearance between the core housing and an interior wall of the U-shaped receptacle. The method also includes translating the core sample through the CT scanner, such that rotation of the rollers enables a translation of the core housing through the U-shaped receptacle.

In some embodiments, the first position is defined by an angle of about 45° with respect to a vertical axis and a horizontal axis of the body. In some embodiments, the second position is defined by an angle of about 45° with respect to a vertical axis and a horizontal axis of the body. In some embodiments, the clearance comprises at least 5 millimeters (mm). In some embodiments, the core sample has a length of up to 6 feet. In some embodiments, the core sample scanning apparatus is coupled to a stationary table located on the second side of the CT scanner. In some embodiments, the method includes generating an image of the core sample using the CT scanner.

In another embodiment, a system is provided that includes a computed tomography (CT) scanner and a CT scanning table located on a first side of the CT scanner, the CT scanning table configured to translate the core sample through the CT scanner. The system also includes a core sample scanning apparatus located at a second side of the CT scanner. The core sample scanning apparatus includes a body defining a U-shaped receptacle, the U-shaped receptacle configured to receive a core housing containing the core sample, a first roller located at a first position on the U-shaped receptacle, and a second roller located at a second position on the U-shaped receptacle. The first roller and second roller are configured to support a weight of the core housing containing the core sample and define a clearance between the core housing and an interior wall of the U-shaped receptacle.

In some embodiments, the first position is defined by an angle of about 45° with respect to a vertical axis and a horizontal axis of the body. In some embodiments, the second position is defined by an angle of about 45° with respect to a vertical axis and a horizontal axis of the body. IN some embodiments, a stationary table located at the second side of the CT scanner, wherein the core sample scanning apparatus is coupled to the stationary table. In some embodiments, the core sample has a length greater than 3 feet.

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

As will be appreciated, an extended length core sample may include samples of extracted subsurface material (for example, rock) that may be taken from a formation having a hydrocarbon reservoir. After extraction, a core sample may be stored in protective containers, transported to a laboratory or other location, and analyzed to evaluate characteristics of the hydrocarbon reservoir or subsurface. The term "core sample" used in the disclosure may refer to the core sample itself, and the core sample may be stored in a protective container (typically a cylindrical container, referred to as a "core housing") that is at least partially transparent to electromagnetic energy. A core housing may be formed from a non-metallic material and may be opaque, translucent, or transparent. In some embodiments, a core sample may include a full diameter sample, a special core analysis (SCAL) sample, a conventional core analysis (CCA) sample, or a mechanical property sample.

Embodiments of the disclosure include methods and apparatuses for imaging an extended length core sample using a CT scanner with fixtures for positioning of core samples. As described in the disclosure, an extended length core sample scanning apparatus may enable the imaging of extended length core samples using medical-type CT scanners. The extended length core sample scanning apparatus may have a frame that defines a U-shaped receptacle configured to receive an extended length core sample within an extended length core housing. The extended length core sample scanning apparatus may have two or more rollers located in the U-shaped receptacle to enable translation of an extended length core sample through the U-shaped receptacle. The rollers may also provide for a minimum clearance between the extended length core sample and the walls of the U-shaped receptacle.

The extended length core sample scanning apparatus may be coupled to a stationary table located on one side of a CT scanner. A moveable CT scanning table may be located on the other side of the CT scanner. One end of the extended length core sample may be coupled to the CT scanning table via a holder, and the other end of the extended length core sample may be received in the U-shaped receptacle of the extended length core sample scanning apparatus. The entire length of the extended length core sample may be imaged by translating the extended length core sample through the CT scanner such that the extended length core sample moves over the rollers and through the U-shaped receptacle of the extended length core sample scanning apparatus.

Figure 1:
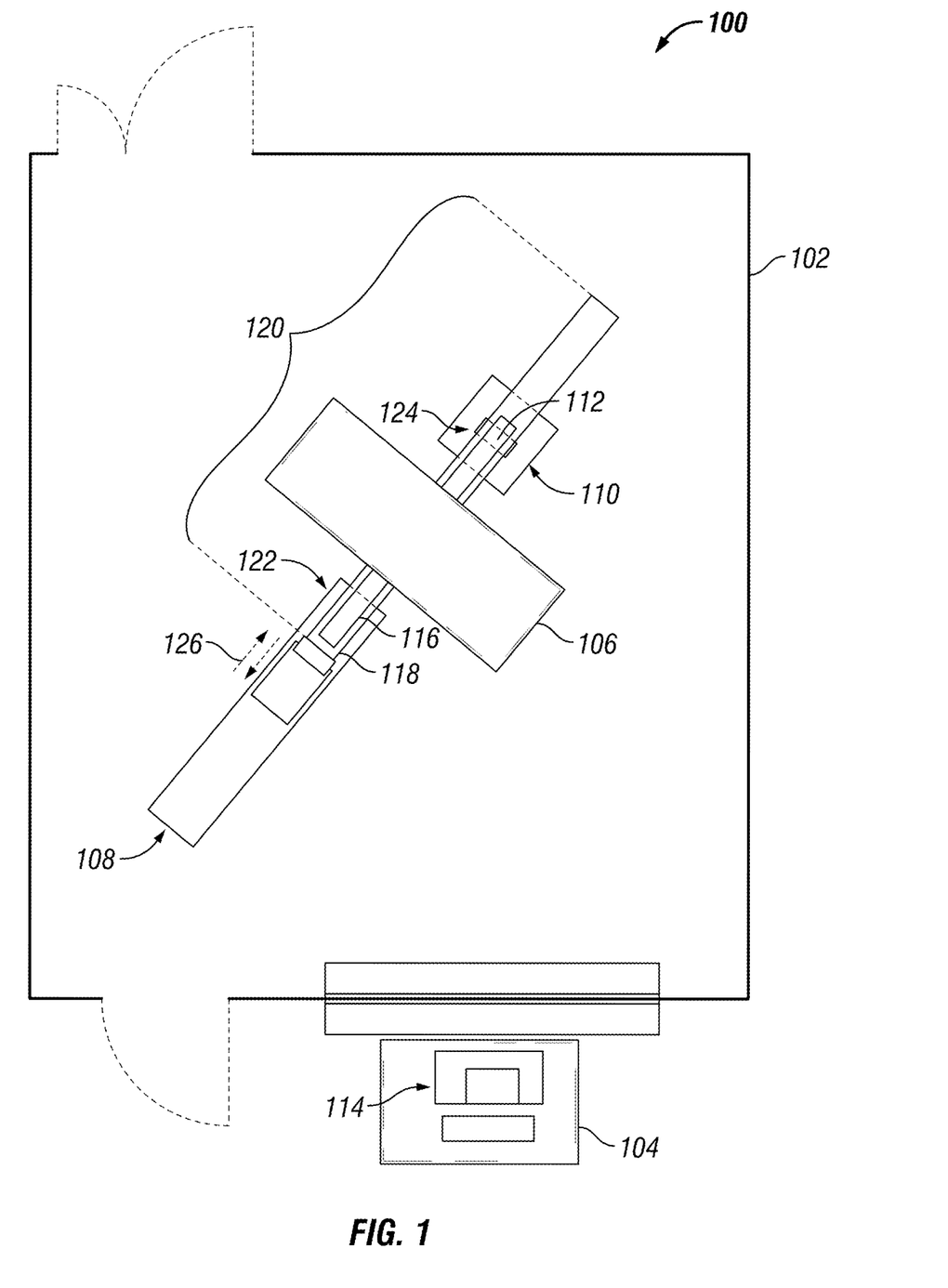
FIG. 1 is a schematic diagram of a computed tomography (CT) scanning environment that includes a CT scanning room and a CT scanning control room in accordance with an embodiment of the disclosure.

FIG. 1 depicts a computed tomography (CT) scanning environment 100 that includes a CT scanning room 102 and a CT scanning control room 104 in accordance with an embodiment of the disclosure. FIG. 1 depicts a CT scanner 106 and a CT scanning table 108 located in the CT scanning room 102. FIG. 1 also depicts a stationary (that is, fixed and non-moveable) table 110 having an extended length core sample scanning apparatus 112 coupled to the table 110 in accordance with embodiments of the disclosure. The CT scanning control room 104 may include a computer 114 that enables control and operation of the CT scanner 106.

As discussed in the disclosure, the extended length core sample scanning apparatus 112 enables scanning of an extended length core sample 116 within a core housing 118. As shown in FIG. 1, the core housing has a length 120. The core housing 118 may be formed from a non-metallic opaque, transparent, or translucent material, such as Plexiglas®. The length of the extended length core sample 116 may be, for example, up to 6 feet (ft) in length. In some embodiments, the core sample length may be less than 6 feet and may be as short as about 3 inches. In some embodiments, the length 120 of the core housing 118 may be up to 3.4 meters (about 11 feet) in length. The extended length core sample scanning apparatus 112 may provide for translation of the extended length core sample 116 enclosed in the core housing 118 through the CT scanner 106 to enable imaging of the entire length (for example, up to 6 feet) of the extended length core sample 116.

To enable scanning of the entire length of the extended length core sample 116 within the core housing 118, one end 122 of the core housing 118 may be fixed to the CT scanning table 108, while the other end 124 of the core housing 118 may be received by the extended length core sample scanning apparatus 112. As shown by arrows 126, the extended length core sample within the core housing 118 may be translated through the CT scanner 106 by translating the CT scanning table 108 back and forth, while the core housing 118 (and extended length core sample 116 within) moves through the extended length core sample scanning apparatus 112.

Figure 2:
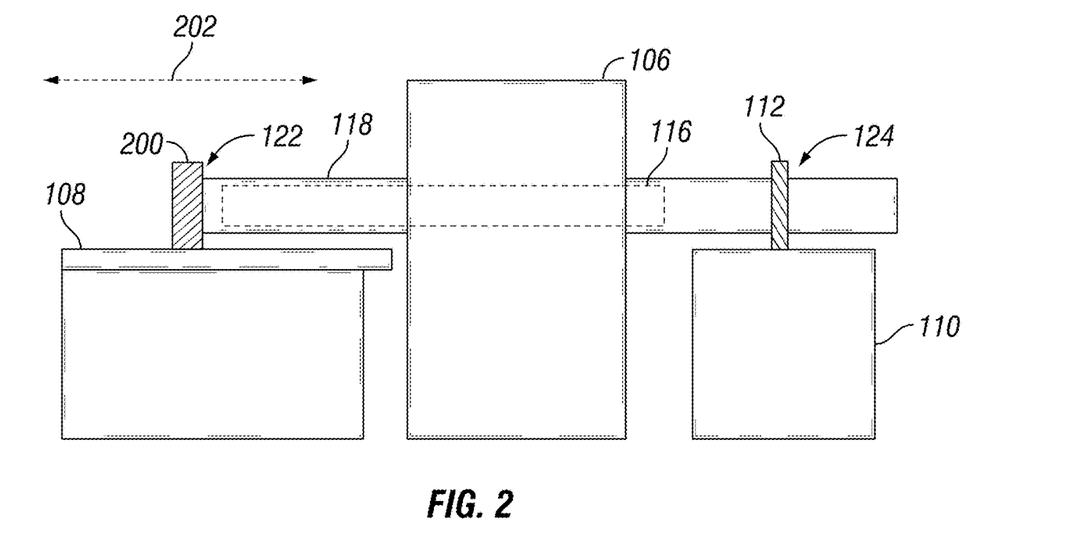
FIG. 2 is a schematic side view of the CT scanner, a CT scanning table, and extended length core sample scanning apparatus of FIG. 1 in accordance with an embodiment of the disclosure.

FIG. 2 depicts a schematic side view of the CT scanner 106, the CT scanning table 108, and extended length core sample scanning apparatus 112 in accordance with an embodiment of the disclosure. As shown in FIG. 2, one end 122 of the core housing 118 may be fixed to the CT scanning table 108 via a holder 200 coupled to the CT scanning table 108. The CT scanning table 108 may translate along the direction shown by arrow 202, such that the core sample 116 also translates along the same direction and through the CT scanner 106.

As also shown in FIG. 2, the other end 124 of the core housing 118 with the extended length core sample is received by the extended length core sample scanning apparatus 112. The extended length core sample scanning apparatus 112 may be coupled to the stationary table 110, such that the table 110 and extended length core sample scanning apparatus 112 do not move when the extended length core sample 116 is translated through the CT scanner 106. As discussed in the disclosure, the extended length core sample 116 may remain received by and move through the extended length core sample scanning apparatus 112 to enable scanning of the entire length of the extended length core sample 116.

Figure 3:
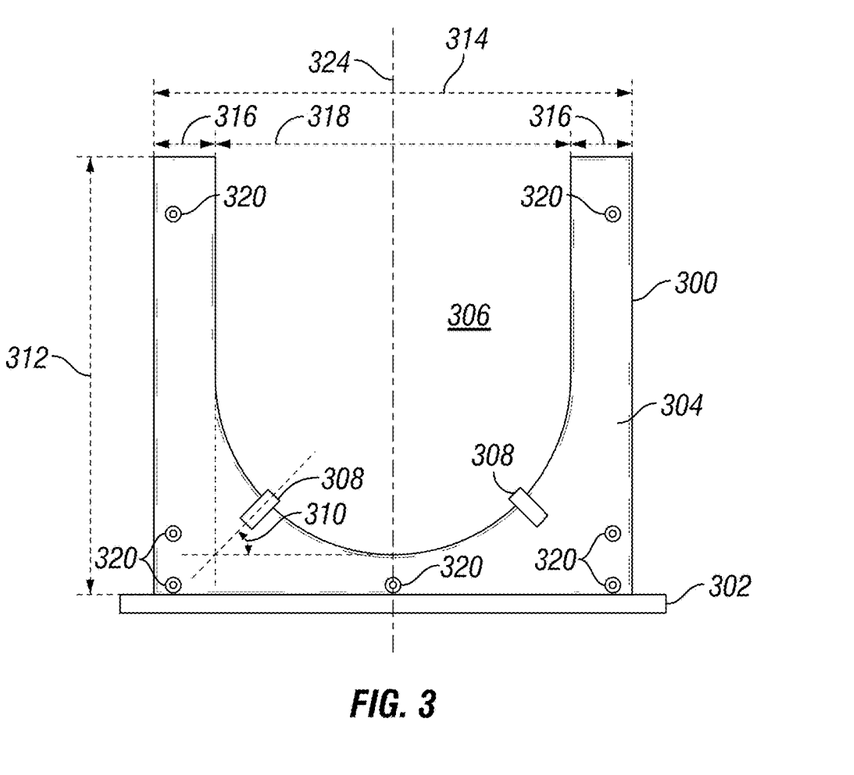
FIG. 3 is a schematic front view of an extended length core sample scanning apparatus in accordance with an embodiment of the disclosure.

FIG. 3 is a schematic front view of an extended length core sample scanning apparatus 300 in accordance with an embodiment of the disclosure. The extended length core sample scanning apparatus 300 may include or be coupled to a base 302. The base 302 may be coupled to a stationary table to enable use of the extended length core sample scanning apparatus 300 with a CT scanner. The extended length core sample scanning apparatus 300 may include a frame 304 that defines a U-shaped receptacle 306 to receive an extended length core sample.

The extended length core sample scanning apparatus 300 may include rollers 308 located in the frame 304. The rollers 308 may be disposed at an angle 310 relative to the vertical and horizontal axes of the frame 304. As shown in FIG. 3, in some embodiments, the extended length core sample scanning apparatus 300 may include two rollers 308 each disposed at an angle of about 45° defined by the vertical and horizontal axes of the frame 304. As discussed in the disclosure, the rollers 308 may support a weight of the core sample received in the U-shaped receptacle such that the core sample rests on the rollers 308 and is translatable over the rollers 308. In some embodiments, the rollers 308 may be formed from plastic or metal.

The U-shaped receptacle 306 and the rollers 308 may be sized to accommodate core samples having a range of diameters and to provide a minimum clearance between a received core sample and the inner wall of the U-shaped receptacle 306. The minimum clearance may ensure that a core sample received in the U-shaped receptacle may freely move through the U-shaped receptacle 308 as the core sample is translated through the CT scanner for imaging.

In other embodiments, the extended length core sample scanning apparatus may include other components that support a weight of the core sample and define a clearance between the core sample and the interior wall of the U-shaped receptacle to enable translation of the core sample through the U-shaped receptacle. For example, in other embodiments the core sample scanning apparatus 300 may include bearings, wheels, or other suitable components.

As shown in FIG. 3, the frame 304 of the extended length core sample scanning apparatus 300 has a height 312 and a width 314. The walls of the U-shaped receptacle 306 have a width 316, such that difference between the width 316 and the width 314 define a width 318 of the U-shaped receptacle 306. Thus, in some embodiments, the width 318 may be equal to the width 314 minus two times the width 316. In some embodiments, the height 312 may be about 11 inches, the width 314 may be about 12 inches (about 305 mm), and the width 316 of the walls may be about 1.5 inches (about 38 millimeters). In such embodiments, the width 318 of the U-shaped receptacle 306 may be about 9 inches (about 229 millimeters).

In some embodiments, the frame 304 may be formed from one or multiple pieces. For example, as shown in FIG. 3, the frame 304 may be formed from multiple pieces coupled together via fasteners 320. The fasteners 320 may include nails, screws, nuts and bolts, or other suitable fasteners known in the art. In some embodiments, the frame 304 may be formed from wood. In other embodiments, the frame may be formed from plastic or other materials.

The U-shaped receptacle 308 may define a vertical axis 324. In some embodiments, when a core sample is received in the U-shaped receptacle 308, the extended length core sample may be positioned such that vertical axis 324 is aligned with the center of a core sample. When a core sample is translated through a CT scanner, the core housing may move over the rollers in a direction perpendicular to the vertical axis 324.

Figure 4:
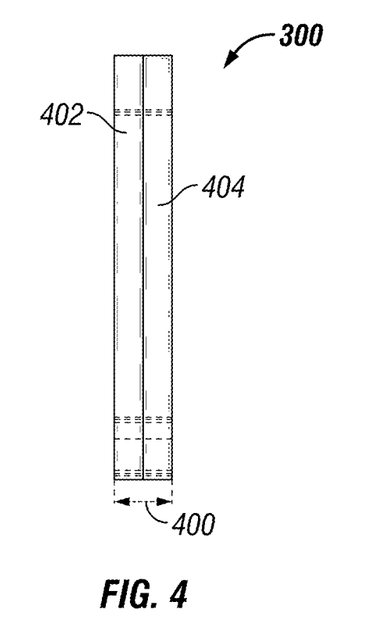
FIG. 4 is a schematic side view the extended length core sample scanning apparatus of FIG. 3 in accordance with an embodiment of the disclosure.

FIG. 4 is a side view of the extended length core sample scanning apparatus 300 in accordance with an embodiment of the disclosure. As shown in FIG. 4, the extended length core sample scanning apparatus 300 has a length 400. In some embodiments, the length 400 may be about 1.5 inches.

The frame 304 may be formed form multiple pieces or a single piece. In some embodiments, multiple pieces may be added to the frame 304 to extend the length 400 of the frame 304. As shown in FIG. 4, the frame 304 of the extended length core sample scanning apparatus 300 may be formed from a first piece 402 and a second piece 404. In other embodiments, the extended length core sample scanning apparatus 300 may be formed from a single piece of material having the length 400.

Figure 5:
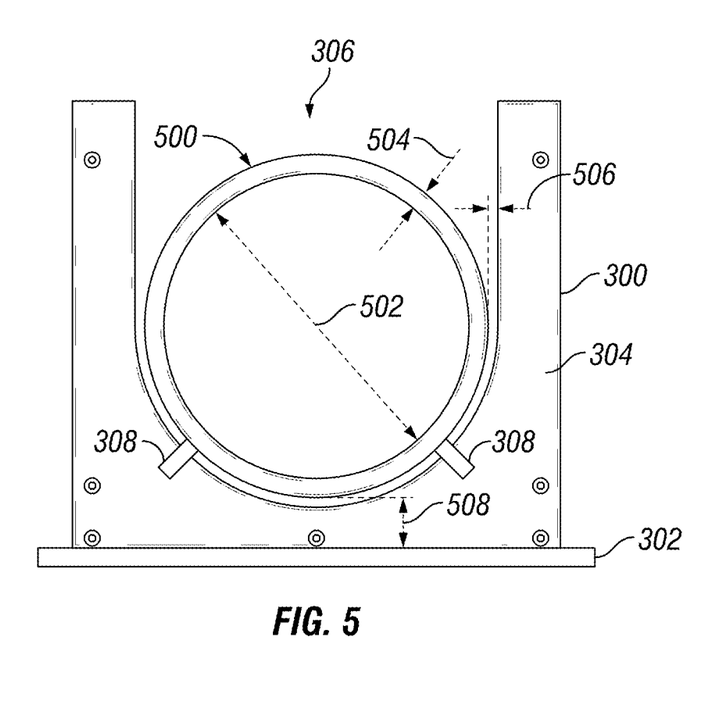
FIG. 5 is a schematic front view of the extended length core sample scanning apparatus with an example extended length core sample received in a U-shaped receptacle in accordance with an embodiment of the disclosure.

FIG. 5 depicts a front view of the extended length core sample scanning apparatus 300 with an example extended length core housing 500 received in the U-shaped receptacle 306 in accordance with an embodiment of the disclosure. The example extended length core housing 500 may include a containing that has an inner diameter 502 and a wall thickness 504. In some embodiments, the example extended length core housing 500 may include a container having an inner diameter 502 of about 7.55 inches and a wall thickness 504 of about 0.5 inches.

As discussed supra, the frame 304 and the rollers 308 of the extended length core sample scanning apparatus 300 may provide for a specific clearance between the outer surface of the example extended length core housing 500 received in the U-shaped receptacle 306. As shown in FIG. 5, when the example extended length core housing 500 is received in the U-shaped receptacle, a clearance 506 may be defined between the example extended length core housing 500 and the interior wall of the U-shaped receptacle 306. In some embodiments, the minimum clearance 506 it about 5 mm. FIG. 5 also depicts the distance 508 between the core housing 500 and the base 302. In some embodiments, the distance 508 is about 30 mm.

Figure 6:
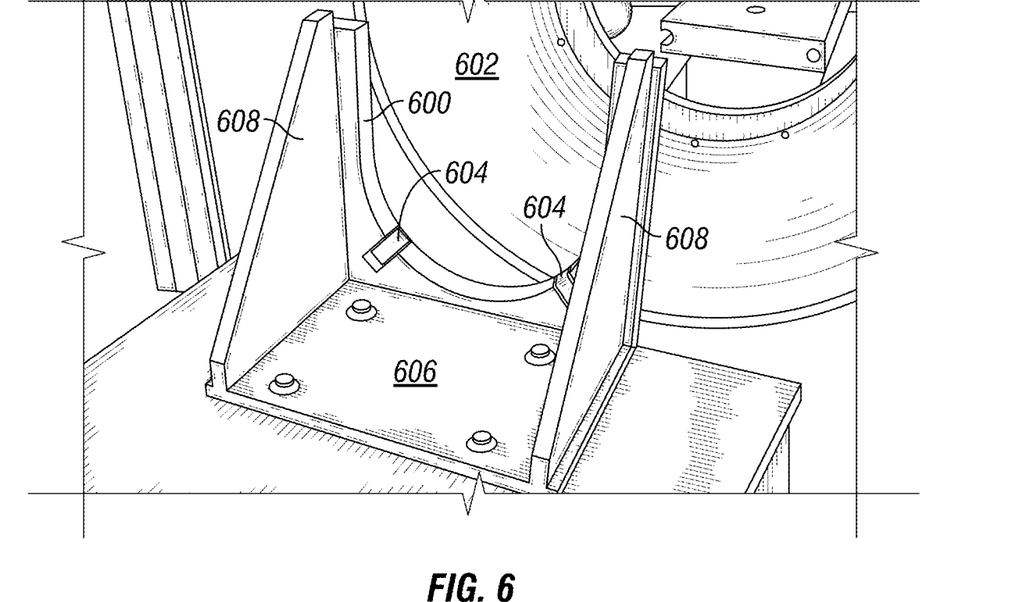
FIG. 6 is a perspective view of an extended length core sample scanning apparatus in accordance with an embodiment of the disclosure.

In some embodiments, an extended length core sample scanning apparatus may be coupled to or include a base for additional stability and for coupling to a stationary table (for example, the stationary table 110 described supra and shown in FIGS. 1 and 2. FIG. 6 is a perspective view of an extended length core sample scanning apparatus 600 in accordance with an embodiment of the disclosure. FIG. 6 depicts a U-shaped receptacle 602 and rollers 604 configured in accordance with the techniques described in the disclosure. Additionally, FIG. 6 depicts a base 606 that may provide additional stability to the extended core length core sample scanning apparatus 600. For example, the base 606 may have walls 608 that may be coupled to the extended length core sample scanning apparatus 600 in the manner shown in FIG. 6 to provide additional stability to the extended length core sample scanning apparatus 600.

Figure 7:
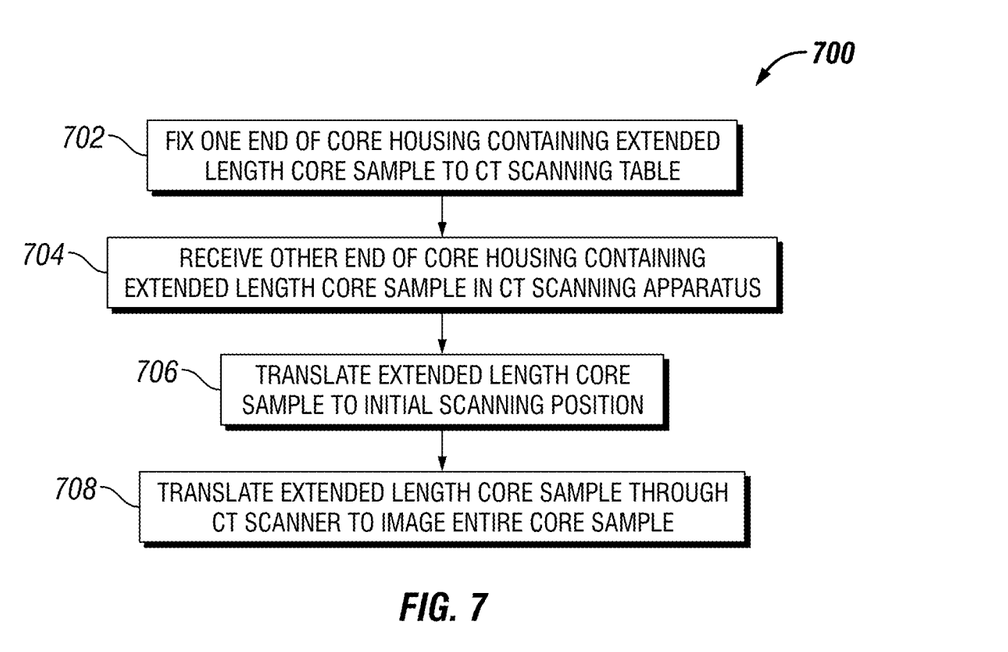
FIG. 7 is a flowchart of a process for scanning a core sample using a CT scanner and an extended length core sample scanning apparatus in accordance with an embodiment of the disclosure.

FIG. 7 depicts a process 700 for scanning a core sample using a CT scanner and an extended length core sample scanning apparatus in accordance with an embodiment of the disclosure. Initially, one end of an extended length core sample may be fixed to a CT scanning table (for example, via a holder described supra) located on one side of a CT scanner (block 702). The other end of the extended length core sample may be received in the U-shaped receptacle of the extended length core sample scanning apparatus located on the other side of the CT scanner (block 704).

After the extended length core sample is positioned for scanning, the extended length core sample may be translated to an initial scanning position in the CT scanner (block 706) by translating the CT scanning table, so that the CT scanning may begin. The extended length core sample may then be translated through the CT scanner to image the entire core sample, such that portions of the extended length core sample move through the U-shaped receptacle of the extended length core sample scanning apparatus (block 708). As the CT scanning table translates, the entire length of the extended length core sample may be imaged by the CT scanner.

Figure 8A:
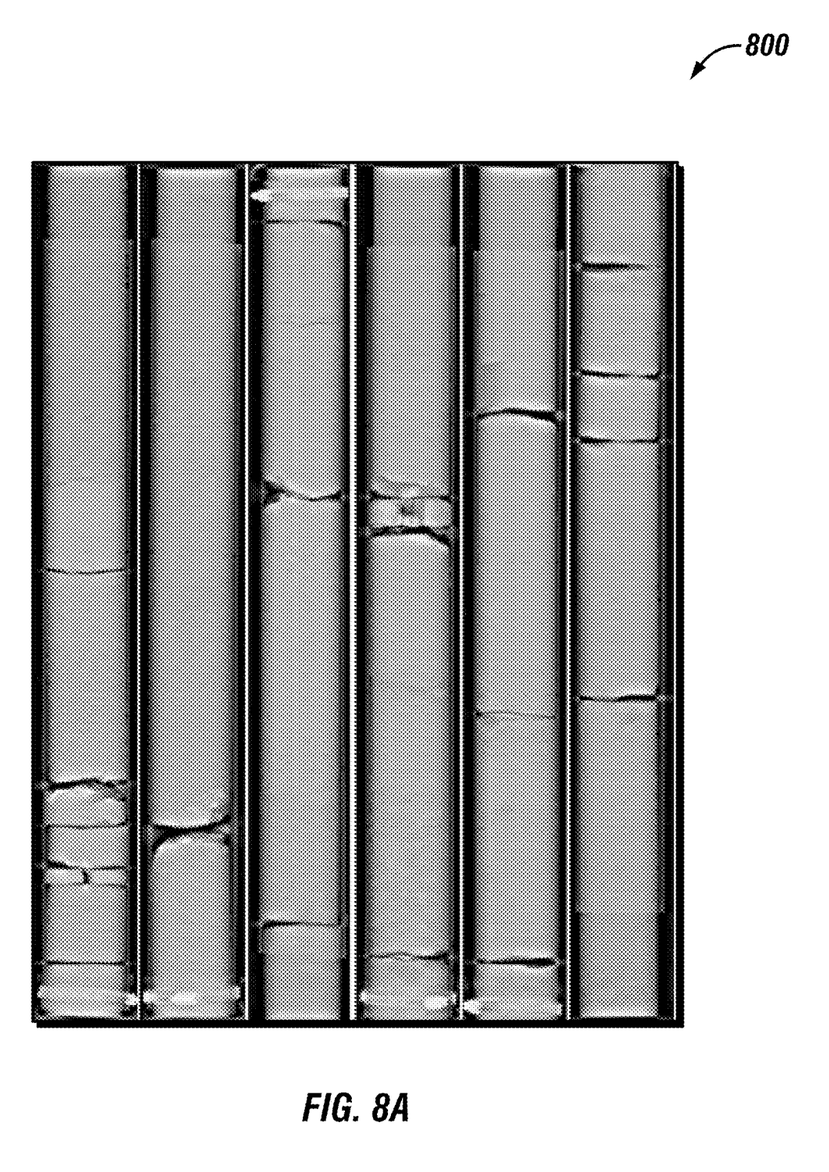
FIGS. 8A and 8B depict images of core samples scanned using a CT scanner and, in some instances, an extended length core sample scanning apparatus in accordance with an embodiment of the disclosure.
Figure 8B:
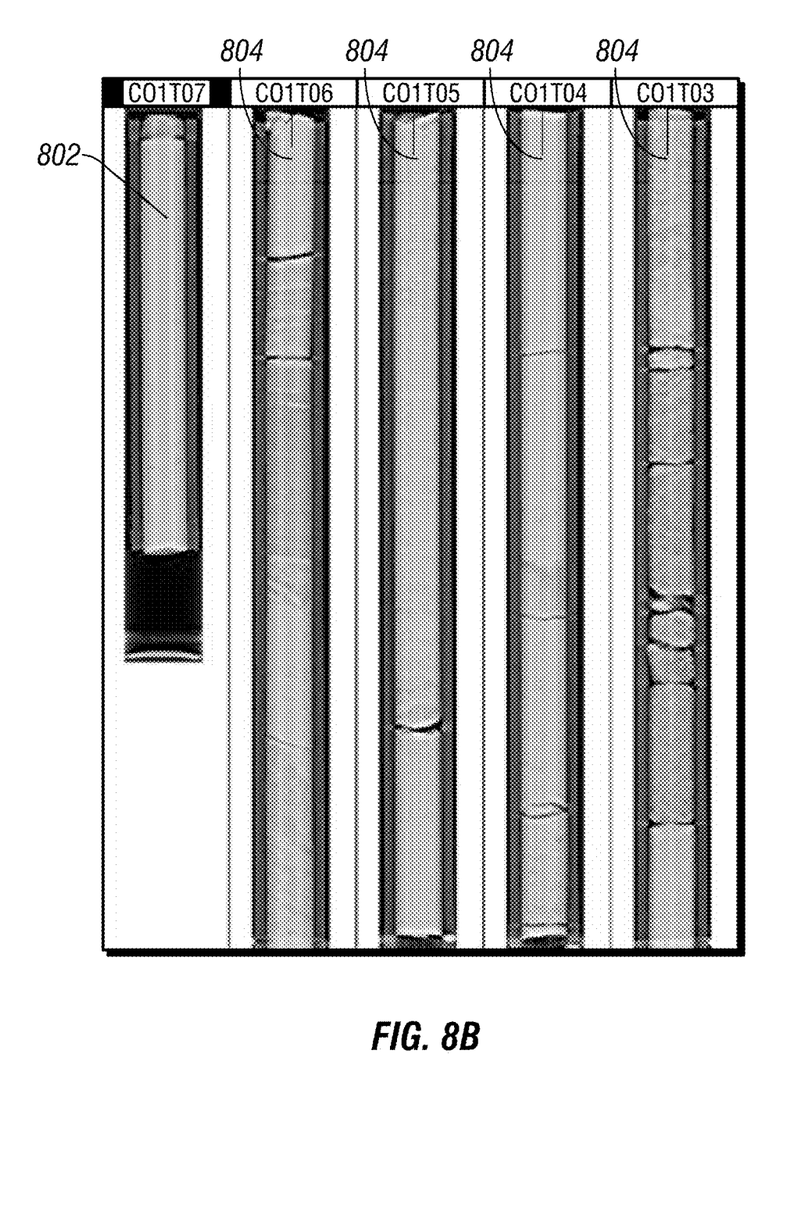

FIG. 8A depict images of core samples of 3 ft in length and scanned using a CT scanner in accordance with an embodiment of the disclosure. FIG. 8A depicts multiple core sample images 800 generated from core samples each having a length of about 3 ft. FIG. 8B depicts images of core samples scanned using a CT scanner and an extended length core sample scanning apparatus in accordance with an embodiment of the disclosure. FIG. 8B depicts a core sample image 802 generated from a core sample having a length of 3 feet (ft) but housed in a core housing capable for containing extended length core samples. The other core samples images 804 depicted in FIG. 8B are generated from extended length core samples each having a length of about 5 ft. As shown in FIG. 8B, the images 802 illustrate the capability of an extended length core sample apparatus as described in the disclosure to enable the scanning of the entire length of an extended length core sample without cutting the core sample into smaller pieces.

The images 800, 802, and 804 may be used, for example, in core analysis planning to determine which core samples to use for further testing, such as by identifying core samples from which to take plugs or other samples and determining the location of such plugs or other samples within the identified core samples. The images 800, 802, and 804 may be used to estimate the type and variations of rock or other substances in the core sample Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. An apparatus for computed tomography (CT) imaging of a core sample, comprising:
    a body coupled to a stationary table located at a first side of a CT scanner, the body defining a U-shaped receptacle external to the CT scanner and configured to receive a core housing containing a core sample;
    a first roller located at a first position in the U-shaped receptacle; and
    a second roller located at a second position in the U-shaped receptacle, the first roller and second roller in contact with the core housing and configured to support a weight of the core housing containing the core sample, wherein the first roller and second roller define a clearance between the core housing and an interior wall of the U-shaped receptacle;
    a moveable table located at a second side of the CT scanner, the second side opposite the first side, wherein translation of the moveable table translates the core housing through the U-shaped receptacle and through the CT scanner,
    wherein a rotation of the rollers enables a translation of the core housing through the U-shaped receptacle and through the CT scanner such that the body is stationary during the translation.

2. The apparatus of claim 1, wherein the first position is defined by an angle of about 45° with respect to a vertical axis and a horizontal axis of the body.

3. The apparatus of claim 1, wherein the second position is defined by an angle of about 45° with respect to a vertical axis and a horizontal axis of the body.

4. The apparatus of claim 1, wherein the clearance comprises at least 5 millimeter (mm).

5. The apparatus of claim 1, wherein the core housing contains a core sample having a length greater than 3 feet.

6. The apparatus of claim 5 wherein the core housing contains a core sample having a length of 6 feet.

7. The apparatus of claim 1, wherein the body is coupled to a support having at least two walls extending in the direction of translation.

8. The apparatus of claim 1, wherein the U-shaped receptacle has a width of 229 millimeters (mm) at a top of the U-shaped receptacle.

\* \* \* \* \*